United States Patent [19]

Goble et al.

[11] Patent Number: 5,411,506
[45] Date of Patent: May 2, 1995

[54] ANCHOR DRIVER

[75] Inventors: E. Marlowe Goble; Alan Chervitz; David P. Luman; Kenneth L. Jensen, all of Logan, Utah

[73] Assignee: Mitek Surgical Products, Inc., Westwood, Mass.

[21] Appl. No.: 225,768

[22] Filed: Apr. 11, 1994

[51] Int. Cl.⁶ .............................................. A61B 17/56
[52] U.S. Cl. ..................................................... 606/104
[58] Field of Search ................ 606/104, 99, 86, 139, 606/148, 232

[56] References Cited

U.S. PATENT DOCUMENTS

| | | | |
|---|---|---|---|
| 4,632,100 | 12/1986 | Somers et al. | |
| 4,738,255 | 4/1988 | Goble et al. | |
| 4,779,616 | 10/1988 | Johnson | |
| 4,946,468 | 8/1990 | Li | 606/232 |
| 5,013,316 | 5/1991 | Goble et al. | 606/72 |
| 5,021,059 | 6/1991 | Kensey et al. | 606/232 X |
| 5,037,426 | 8/1991 | Goble et al. | 606/96 |
| 5,071,420 | 12/1991 | Paulos et al. | 606/99 |
| 5,100,417 | 3/1992 | Cerier et al. | 606/139 |
| 5,102,421 | 4/1992 | Anspach, Jr. | 606/232 |
| 5,139,520 | 8/1992 | Rosenberg | 623/13 |
| 5,207,679 | 5/1993 | Li | 606/72 |
| 5,211,650 | 5/1993 | Noda | 606/139 |
| 5,224,946 | 7/1993 | Hayhurst et al. | 606/72 |
| 5,236,445 | 8/1993 | Hayhurst et al. | 606/232 |
| 5,258,016 | 11/1993 | DiPoto et al. | 606/232 |

Primary Examiner—Tamara L. Graysay
Attorney, Agent, or Firm—M. Reid Russell

[57] ABSTRACT

An anchor driver for mounting a ligament anchor and turning it into a bone, which ligament anchor includes a suture attached to a rear end that is maintained in a driver body until the anchor driver is pulled off of the ligament anchor seated in the bone. The driver body is preferably a rigid straight tube that includes an anchor mount disposed on a forward end whereto the ligament anchor is fitted. So arranged, a suture, that is disposed on the ligament anchor coupling end, will extend therefrom as a suture strand or strands that are fitted through the anchor mount, to pass through the driver body and are then bent to double back upon themselves and fitted back into the driver body. For maintaining the suture strand or stands in a straight attitude, in one embodiment a resilient cap is provided that has a hole or slot formed therein wherethrough the suture strand bend or bends are fitted into a cavity within the cap, which cap is then fitted over the driver body open end. With, in another embodiment, a grommet and thin walled tube are disposed end to end in the driver body wherethrough the suture strand or strands are fitted that are then bent to double back alongside the tube, and are maintained within the driver body, which driver body then receives a cap fitted over an open rear end thereof.

6 Claims, 3 Drawing Sheets

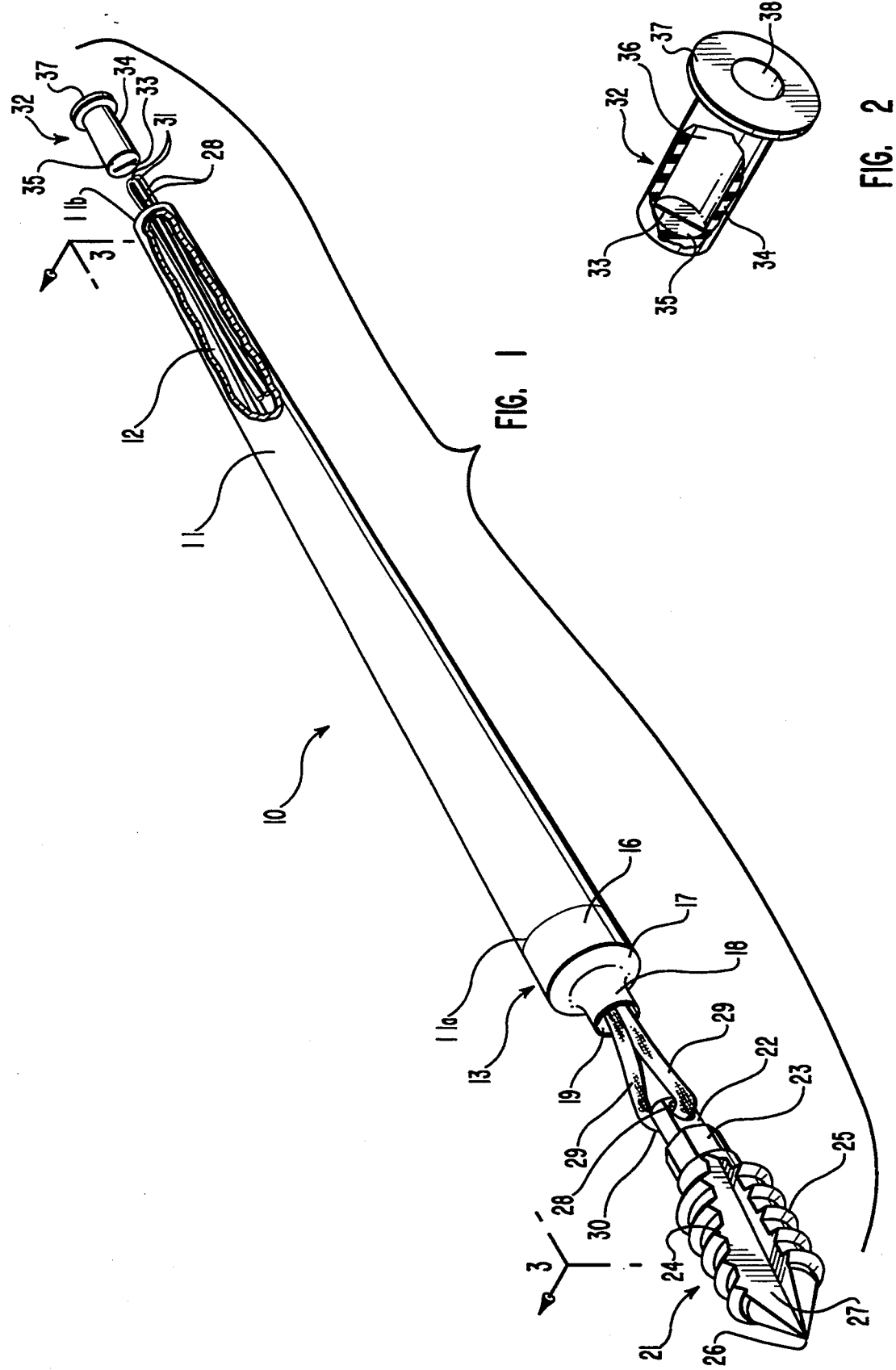

ANCHOR DRIVER

BACKGROUND OF THE INVENTION

1. Field of the Invention

This invention relates to medical equipment and in particular to drivers for use in installing an anchor device into a bone for maintaining a ligament section thereto.

2. Prior Art

Driver devices for use in both positioning and fixing an anchor or fastener onto a bone surface location whereat a ligament section, or the like, is to be attached are well known. An earlier invention of one of the present inventors in a Suture Anchor Assembly, U.S. Pat. No. 4,632,100, shows a driver for mounting an anchor on a forward end thereof, with a suture connected to the anchor rear end that is shown contained in a driver center cavity. The driver of the U.S. Pat. No. 4,632,100, like those of the present invention, provides for guiding an anchor mounted onto a driver forward end to a bone location and for turning that mounted anchor into a bone cortex. Whereafter, the driver is pulled off of the anchor, exposing a suture that is connected to the anchor end and is maintained within the driver body. Distinct therefrom, the ligament anchor driver of the invention provides an arrangement for maintaining the suture contained within the driver body as a pair of straight suture strands that are bent upon themselves, facilitating the driver being pulled away. Such driver separation is made without the suture strands twisting or knotting together as could hamper driver removal from the seated anchor.

A use of the anchor and driver of the above cited U.S. Pat. No. 4,632,100 is shown in another patent to one of the inventors, U.S. Pat. No. 5,037,426. Also, U.S. Pat. Nos. 4,738,255 and 5,013,316, to one of the present inventors, illustrate other driver and anchor combinations. Additionally, a number of combinations of anchors and drivers with arrangements for capturing, maintaining and fitting sutures to extend from seated anchors are shown in U.S. Pat. Nos. 4,779,616; 4,946,468; 5,071,420; 5,100,417; 5,102,421; 5,139,520; 5,207,679; 5,211,650; 5,224,946; 5,236,445; and 5,258,016. None of which patents, however, involves an anchor driver with an arrangement for maintaining a suture within the driver body that is like that of the invention.

SUMMARY OF THE INVENTION

It is therefore, a principal object of the present invention to provide a driver for maintaining an anchor on a forward end thereof for mounting in a bone cortex, which anchor includes a suture extending from its rear end that is contained in the driver body to freely pass out of the driver body as the driver is pulled away from the anchor seated in bone cortex.

Another object of the present invention is to provide a driver that includes a center longitudinal cavity that is to maintain a suture folded upon itself therein, which suture is arranged to travel freely out of a narrow opening in the driver end as it is pulled off of an anchor rear end.

Another object of the present invention is to provide for arranging in the driver longitudinal cavity to maintain at least one suture as a single pair or number of straight strands that are folded upon itself or themselves until the driver is pulled off from the anchor whereupon the suture strand or strands will unfold to travel freely out from the driver end.

Still another object of the present invention is to provide, in two driver embodiments, arrangements within the driver longitudinal cavity for maintaining the suture contained therein as a straight strand or strands that is or are folded upon themselves, and provides for guiding suture travel out from a driver end narrow opening so as to prevent the suture strand or strands from knotting or twisting on itself or each other as the driver is pulled away from the seated anchor rear end.

Still another object of the present invention is to provide a driver and anchor combination for convenient packaging together as a unit.

In accordance with the above objects, the present invention in a ligament anchor driver includes a driver body that is a straight section that is, preferably, formed, from a metal, such as stainless steel, that is suitable for use in a surgical procedure practiced on a human. The body is preferably cylindrical and includes a center longitudinal cavity that opens through a narrow opening into a drawer forward end that is formed as an anchor mount. The anchor mount is preferably a cylindrical collar that has a sided inner circumference to accommodate a sided outer surface of an anchor rear coupling end with the driver forward end narrow opening formed axially through the collar center into the driver cavity. Preferably, the anchor rear coupling end is formed to have a multi-sided cross section as its connection surface, and is for fitting into the collar and engaging the collar inner side walls that preferably have a hexagon cross section.

For the invention, a suture that may be a single strand but is preferably folded upon itself into two or more strands, is attached to the anchor rear end. So arranged, the end or ends of the suture strand or strands will extend from the anchor rear end to be passed through the driver narrow opening and extend through the driver and may be pulled to draw the anchor rear coupling end into the driver cylindrical collar. In one embodiment of the invention, the suture strand or strands is or are folded upon itself or themselves at approximately the point of exit from the driver open rear end.

The suture strand or strands folds in a first embodiment are fitted into a slot that is formed across an end surface of a resilient cap. The resilient cap is to fit into and close over the driver open rear end. With the suture strand or strands folds maintained in the resilient cap, the end or ends of the straight suture strand or strands are fitted back into the driver center longitudinal cavity, and the resilient cap is fitted over the driver open end. So arranged, the straight suture strand or strands, that have been folded on themselves, are maintained within the driver until the driver is pulled off from the anchor after it is seated in a bone cortex. Thereupon, the straight suture strand or strands will be pulled from the resilient cap slot to unfold and the suture straighten out to travel through the driver narrow opening as the driver is removed.

A second embodiment of the invention is like the first embodiment, as set out above, except that, the driver includes a grommet and tube that are disposed in the driver center longitudinal cavity. The grommet is positioned adjacent to the anchor mounting end may be tightly or loosely fitted therein to turn around its longitudinal axis, and has an axial opening formed therethrough and further may be slotted to open that longitudinal opening from end to end to receive the straight suture strand or strands fitted therethrough. The straight suture strand or strands are to extend through the grommet opening and through a tube that may be disposed in the driver cavity or, the grommet may be of a length to extend the length or the driver center longitudinal opening, eliminating a need for a tube. In practice, the straight suture strand or strands are bent at the tube end and fitted back along the tube outer surface. The bent or folded straight suture strands are maintained in the driver cavity by closing off the cavity end, as by installing a cap or cover over that driver cavity open end.

Both first and second embodiments of the ligament anchor driver of the invention provide for maintaining, in a center longitudinal cavity, a straight suture strand or strands bent upon themselves but where suture strands are otherwise straight to facilitate their traveling freely, without twisting or knotting, through the driver narrow end opening. So arranged, the suture strand or strands remain straight to pass freely through the driver narrow opening after the driver has been used to position and mount the anchor into a bone location.

BRIEF DESCRIPTION OF THE DRAWINGS

These and other objects and features of the invention will become more fully apparent from the following description, in which the invention is described in detail in conjunction with the accompanying drawings. In which drawings:

FIG. 1 is a side elevation perspective view of a first embodiment of an anchor driver of the invention showing an anchor with an attached suture exploded from a driver forward end, and showing a section of a driver body rear portion broken away to expose a pair of suture strands bent back upon themselves, with the suture strands bends shown aligned for fitting into a slot that is formed into a bottom face of a cap that is shown aligned for fitting over a driver body open rear end;

FIG. 2 is a side elevation expanded perspective view of the cap of FIG. 1 from a head end thereof, and showing the cap as hollow and formed from a resilient material;

DETAILED DESCRIPTION

Figure 3:
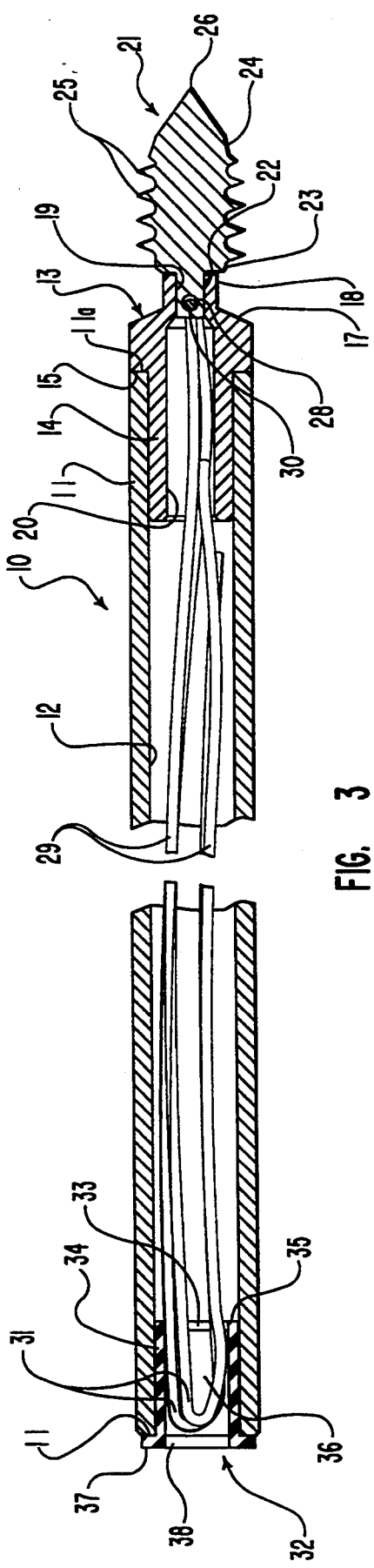
FIG. 3 is a side elevation sectional view taken along the line 3—3 of FIG. 1, showing the anchor fitted onto the forward end of the driver body, with the cap shown fitted over the driver body rear end, and showing the folded suture strands maintained within the driver body.
Figure 5:
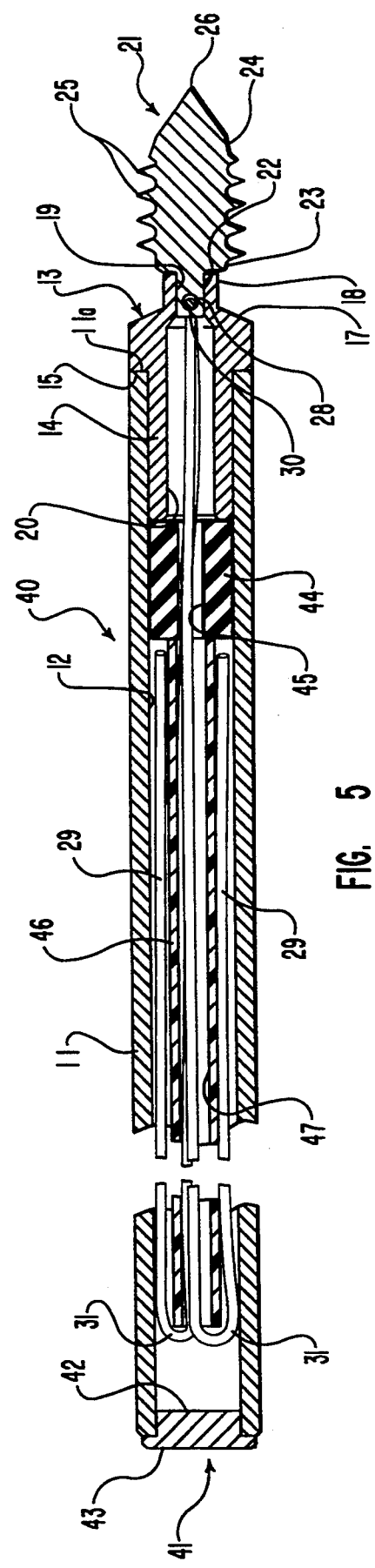
FIG. 5 is a side elevation sectional view taken along the line 5—5 of FIG. 4 that is like FIG. 3, showing the anchor fitted onto the driver forward end, with the grommet and tube shown maintained in the driver body cavity wherethrough the suture strands are fitted and are separated and folded back along the tube side, and showing a cap or crown fitted over the driver body open rear end.
Figure 4:
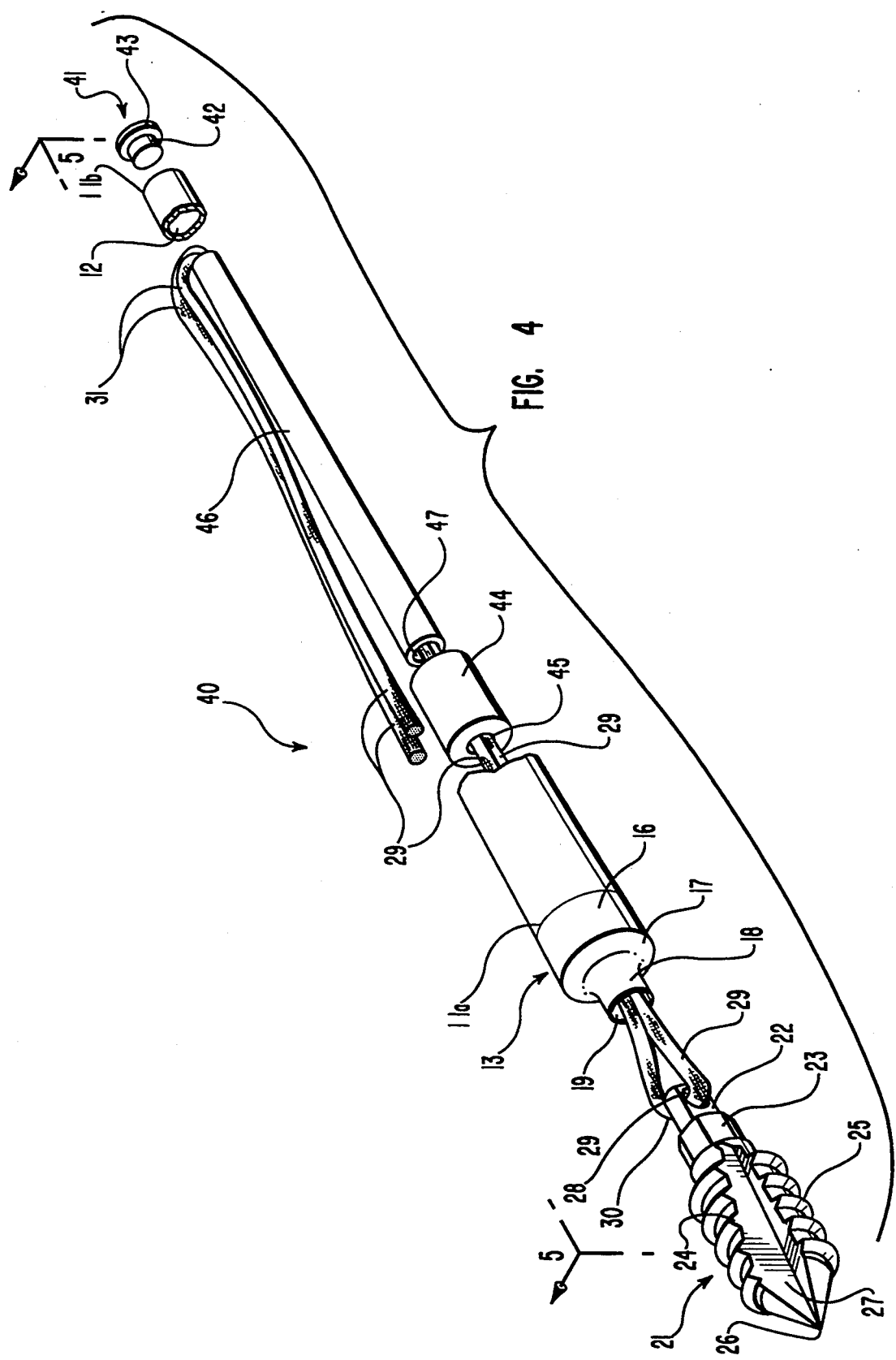
FIG. 4 is view like that of FIG. 1 only showing a second embodiment of an anchor driver of the invention, with an anchor and attached suture shown exploded off of the driver forward end, showing a rear section of the driver body removed to expose a grommet and a tube disposed axially therein wherethrough the suture stands are fitted and are folded back along the tube, and showing a cap or crown for fitting over the driver body open rear end.

The present invention is in an anchor driver 10, that is shown as a first embodiment in FIGS. 1 and 3, and a second embodiment of an anchor driver 40, is shown in FIGS. 4 and 5. Both the anchor drivers 10 and 40, each preferably include a body 11, that is shown as cylindrical, and has a center longitudinal cavity 12 formed therethrough. Though, it should be understood, a body configuration other than cylindrical could be so used within the scope of this disclosure. A forward end 11a of the body 11 is capped by an anchor mount 13 that is preferably formed from a solid section to have, as shown best in FIGS. 3 and 5, a tube end 14 of a diameter to fit snugly into the driver body cavity end 11a, to seat therein. The anchor mount 13 is shown stepped at a right angle outwardly into a step 15 that has approximately the same width as the thickness of the body 11 wall. The anchor mount step 15 end is a base of a head 16 that has approximately the same diameter as does the body 11, and, when mounted thereto, forms a forward end extension of the body end 11a. The anchor mount head 16, at a top end 17, slopes inwardly into a center collar 18, that extends axially therefrom, and includes a center longitudinal coupling hole 19. The coupling hole 19 is open to a center opening 20 that is formed longitudinally through the tube end 14 that, in turn, is open to the body 11 center longitudinal cavity 12.

The anchor mount 13 tube end 14 is for permanent seating in the body forward end 11a, as shown in FIGS. 3 and 5, and the coupling hole 19, as shown best in FIGS. 1 and 4, is preferably sided to present, in cross section, a number of flat surfaces connected at their edges, to form coupling hole 19. Coupling hole 19 preferably has a hexagon cross section to receive a sided coupling end 22 of a ligament anchor 21, hereinafter referred to as anchor. Anchor 21 is preferably a suture anchor like that shown in U.S. Pat. No. 4,632,100, of one of the present inventors, that provides a self drilling and tapping suture anchor for turning into a bone surface. Like the suture anchor, anchor 21 preferably includes a sided coupling end 22 that extends axially from a rear end 23 of a cylindrical anchor body 24 and has outwardly extending threads 25 formed therealong from the rear end 23 to a sloping forward end, terminating in a point 26. A longitudinal flute 27 is formed in the anchor body 24 surface from point 26 to rear end 23 that has a forward edge adjacent to point 26 that is formed as a cutting edge. The combination of the point 26 and flute 27 edge form a fluted drill that is for drilling a hole into a bone surface. The anchor threads 25 as the anchor penetrates the bone hole to engage and turn into the edge of the hole, permanently seating the anchor 21 therein. It should however be understood that the invention is not limited for use with anchor 21 and that another anchor arrangement mounting a suture, or the like, that is for turning, or otherwise arranged for mounting, in a bone cortex can be used with the invention, within the scope of this disclosure.

A hole 28 is provided in the anchor 21 coupling end 22 for receiving a suture 29, or the like, threaded therethrough to preferably provide a single section or equal lengths of suture 29 sections or strands extending from the anchor coupling end, shown as a bend 30 for a pair of suture strands. The suture strand or strands, hereinafter referred to as strands of driver 10, are shown in FIGS. 1 and 3 fitted through the anchor body longitudinal cavity 12 and are bent back upon themselves at 31 and disposed within the cavity. So arranged, the suture 29 strands, to and from their bends 31 are straight and will pull smoothly out of the driver body coupling hole 19 when the driver 10 is pulled off of the anchor 21 after it is seated in a bone.

A resilient cap 32, as shown best in FIG. 2, is provided for receiving the suture strands bends 31 fitted through a diagonal slot 33 that is formed across a flat forward face 35 of a cap sleeve 34. The strand bends are to pass into a cap cavity 36 and are retained within the cap sleeve. The cylindrical cap sleeve 34 has an appropriate diameter to snugly fit into the driver body end 11b that opens into the longitudinal cavity 12, capping off that opening.

The cap sleeve travels into the cavity 12 to where an undersurface of a head shown as a narrow disk 37 that is secured across the cap sleeve engages the driver body end 11b. The cap sleeve cavity 36 houses the suture strands at their bends 31, with the opposing resilient slot 33 edges providing a biasing towards one another to clamp together to resist passage of the suture strands back out of the cavity until the driver 10 is pulled off of the seated anchor 21. Where a single section of a suture 29 is employed it may be bent at intervals therealong back upon itself with the bends at the driver body end 11b to fit through the cap slot 33, as described above. In practice, as the driver 10 is pulled away from anchor 21 that mounts the suture 29 contained at bends 31 in cap 32 are pulled sequentially therefrom as the suture is pulled out of the driver.

To facilitate grasping the suture strands at bends 31 so as to pull them into the cap sleeve cavity 36, a hole 38 is preferably formed through the center of narrow disk 37 that opens into the cavity 36 wherethrough a wire with a hook end, or the like, not shown, can be fitted. The hook end is to receive the suture stands bends 31 and pull them through the slot 33. So arranged, the suture strands, at their bends 31 are maintained in the resilient cap 32 until pulled therefrom, to pass through the driver body longitudinal cavity 12 and out the hole 19 when the driver 10 is pulled off of the anchor 21.

The second embodiment of the driver 40 of the invention is shown in FIGS. 4 and 5. As set out above, driver 40 is like driver 10, as described above and includes the same components except as to the arrangement for maintaining the suture 29 contained in the straight driver body 11 longitudinal cavity 12. As with driver 10, the driver body 11 of driver 40 receives the described anchor mount 13 fitted into end 11a that is for mounting the anchor 21, or other appropriate anchor, and includes the sided coupling end 22 wherethrough a hole 28 is formed that receives suture 29 threaded therethrough. Driver 40 is arranged to mount to anchor 21 and receive a suture section or pair of suture 29 strands fitted through the anchor mount 13 hole 19, passing through the driver body cavity 12 and are bent upon itself or themselves and fitted back into the cavity. The cavity 12 opening at driver end 11b of driver 40 is preferably covered over by a cap 41. Distinct from the cap 32 of driver 10, cap 41 that is for closing over the cavity opening, is preferably a solid section and is formed of a somewhat resilient material. Cap 41 includes a cylindrical end 42 that is of a diameter to snugly fit into the cavity 12 end opening to where an undersurface of a head end, shown as a flat disk 43 maintained across a cylinder 42 top end, engages the driver body end 11b with the cap 41 cylinder 42 fully installed in the cavity opening.

Driver 40 further distinguished from driver 10 in that is includes a grommet 44 disposed axially within the driver body cavity 12, adjacent to the end of the anchor mount tube end 14. The grommet 44 includes a center longitudinal opening 45 formed therethrough that the suture 29 section or strands are fitted through. The grommet may be loose to turn freely in the cavity arranged to fit tightly therein, and may extend the length of the cavity 12. The grommet longitudinal opening 45 may be slotted longitudinally to facilitate the suture 29 being fitted therein within the scope of this disclosure. Alternatively, as shown best in FIG. 4, a thin walled tube 46 may also be disposed within the driver body cavity 12, axially with a short grommet 44. As shown, tube 46 includes a longitudinal opening 47 wherethrough the suture strands are fitted. The suture 29 strands, as shown best in FIG. 5, are bent upon themselves at 31 and the individual stands are arranged alongside the grommet 44 and the tube 46, within the driver body cavity 12. The suture strands are so maintained alongside tube 46 until the driver 40 is pulled off of anchor 21 that has been seated in a bone, as set out above.

While preferred embodiments of our invention in anchor drivers have been shown and described herein, it should be understood that the present disclosure is made by way of example only and that variations to the invention and its use are possible within the scope of this disclosure without departing from the subject matter coming within the scope of the following claims, and a reasonable equivalency thereof, which claims we regard as our invention.

We claim:

1. An anchor driver comprising, a driver body that is a straight section of a rigid material with a center opening therethrough; an anchor mount for seating in a distal end, as a forward extension of, said driver body, which said anchor mount is open longitudinally and includes a distal end arranged to couple to a mounting end of a ligament anchor means arranged for mounting in a hole formed in a bone, which said ligament anchor means mounting end includes a means for securing a suture thereto as, at least, a single suture strand that is for fitting through said anchor mount and driver body open proximal end for folding back upon itself and fitting back through said driver body proximal end; and means for maintaining said suture in a straight attitude to its bend and back upon itself within said driver body that includes a cap means for closing over the driver body open proximal end that includes opposing jaw means for receiving and releasably gripping said suture strand bend therebetween; and means for biasing said Saw means to a closed attitude.

2. An anchor driver as recited in claim 1, wherein the cap means is formed from a resilient material and includes a forward section that is closed across a forward face and is arranged to fit snugly into the driver body open proximal end, and has a slit formed across a said forward face of said cap means forward section, which said slit edges form the opposing jaw means, and said cap means includes a flat section disposed across a proximal end of said forward section that includes a center opening into an open interior of said cap means forward section.

3. An anchor driver as recited in claim 1, wherein the means for maintaining the suture in a straight attitude additionally includes a tube means that is open longitudinally therethrough and is disposed within the driver body to receive said suture fitted therethrough, said suture to exit a rear end of said tube means and is bent back alongside said tube means.

4. An anchor driver as recited in claim 1, wherein the means for maintaining the suture in a straight attitude additionally includes a grommet means disposed in the driver body, adjacent to the anchor mount distal end, and said grommet means includes a center longitudinal passage therethrough.

5. An anchor driver as recited in claim 4, further including a straight tube section disposed within the driver body, axially to the grommet means, said straight tube section including a center longitudinal hole formed therethrough that aligns with the center longitudinal passage formed through said grommet means.

6. An anchor driver as recited in claim 4, wherein the grommet means is loosely fitted into the driver body.

* * * * *